United States Patent [19]

Van Hardeveld

[11] 4,408,046

[45] Oct. 4, 1983

[54] PROCESS OF PREPARING MELAMINE

[75] Inventor: Rudolf Van Hardeveld, Geleen, Netherlands

[73] Assignee: Stamicarbon, B.V., Geleen, Netherlands

[21] Appl. No.: 368,971

[22] Filed: Apr. 16, 1982

[30] Foreign Application Priority Data

Apr. 7, 1982 [NL] Netherlands .......................... 8201479

[51] Int. Cl.³ ............................................ C07D 251/60
[52] U.S. Cl. ................................................... 544/201
[58] Field of Search ......................................... 544/201

[56] References Cited

U.S. PATENT DOCUMENTS 3,496,176 2/1970 Kennedy .......................... 260/249.7
3,598,818 8/1971 Krekels .......................... 260/249.7 P
4,156,080 5/1979 Van Hardeveld .................. 544/201

Primary Examiner—John M. Ford

[57] ABSTRACT

An improved process for the preparation of melamine from urea or thermal decomposition products thereof. A melamine containing reaction mixture is cooled with an aqueous medium to form an aqueous product stream containing melamine and reaction by-products. Product melamine is separated from the aqueous product stream leaving a residual aqueous stream which is recycled into the process. A portion of this residual aqueous stream still containing reaction by-product is treated to remove by-products therefrom prior to being recycled to the process.

12 Claims, 1 Drawing Figure

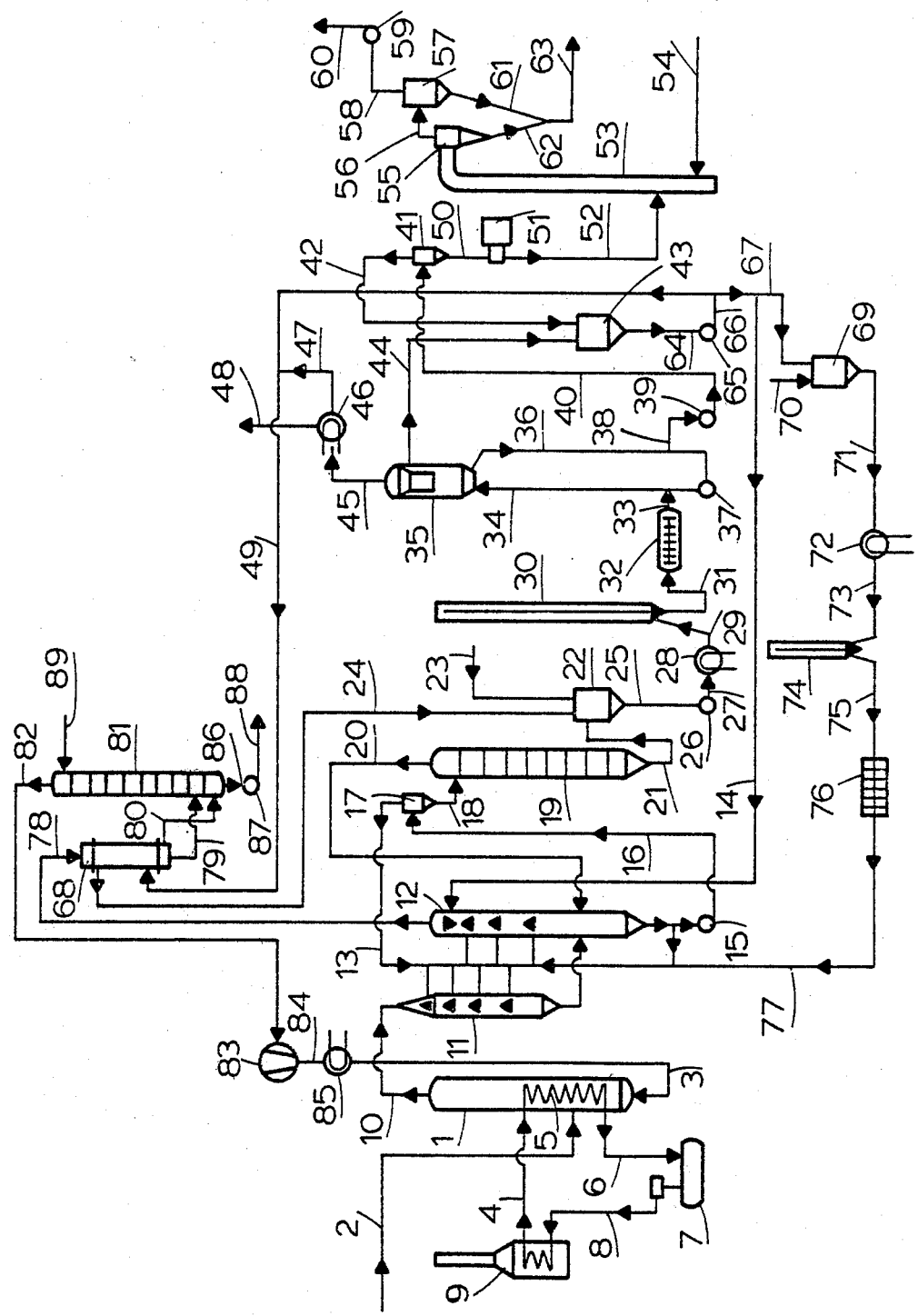

PROCESS OF PREPARING MELAMINE

BACKGROUND OF THE INVENTION

This invention relates to an improved process for preparing melamine by the conversion of urea or thermal decomposition products thereof, wherein a reaction mixture formed in the conversion is cooled with water or an aqueous medium to form an aqueous product stream containing dissolved or suspended melamine. Solid melamine product is subsequently separated from the aqueous product stream leaving a residual aqueous stream. Since this residual aqueous stream, generally mother liquor remaining after crystallization, still contains some quantity of product melamine, it is desirable to recycle the stream into the melamine process, rather than simply discharging it to waste. However, this residual aqueous stream also contains reaction by-products such as ammeline and ammelide, and if the concentration of these by-products is permitted to build up in the recycled steam, they will contaminate the melamine product crystallized out. It is, therefore, necessary to purify this residual aqueous liquid at some point in its recycle in order to obtain melamine of an acceptable purity.

Such a process is known from U.S. Pat. No. 3,496,176 wherein the residual aqueous liquid remaining after crystallization and removal of solid melamine product is first stripped of ammonia and cooled, and thereafter by-products such as ammeline and ammelide are caused to precipitate by acidification using carbon dioxide or some other acid. The precipitated ammeline and ammelide are removed by filtration, after which the filtrate can be recycled and used for cooling a further quantity of reaction mixture.

Although this known process is capable of preventing a by-product buildup in the recycle stream, the energy consumed in carrying out this purification is rather high. It is, therefore, an object of the present invention to prevent the buildup of reaction by-products in the recycled residual aqueous stream at a significantly lower energy consumption than the prior art, while maintaining acceptable levels of melamine product purity.

SUMMARY OF THE INVENTION

It has now surprisingly been found that the buildup of by-product impurities in the recycle can be stabilized by subjecting only a relatively small portion of this liquid stream to a purification treatment, thereby substantially reducing energy requirements while at the same time producing a melamine end product having very few if any impurities.

Specifically, the invention is an improved process for the preparation of melamine from urea or thermal decomposition products thereof wherein a reaction mixture is cooled with an aqueous medium to form an aqueous product stream containing melamine and reaction by-products. Product melamine is separated from this aqueous product stream leaving a residual aqueous stream for recycle into the process, for instance as aqueous medium used to cool a further quantity of the reaction mixture. The improvement involves separating a portion of the residual aqueous stream, still containing reaction by-products, from the remainder of such stream and treating that portion in order to remove by-products prior to recycling it into the process.

The residual aqueous stream normally still contains some amount of ammonia, and thus has a relatively high pH. The purification treatment preferably comprises lowering the pH of the portion of this stream to be purified to a pH value of between about 7.5 and 9.0 by the addition of an acid. At this lower pH level, the solubility of the impurities, such as ammeline and ammelide, is lowered sufficiently that they precipitate. This precipitate is then filtered out of the treated residual aqueous solution prior to its recycle into the process. Preferably, the acidification is effected by the introduction of carbon dioxide, inasmuch as carbon dioxide is already present in the system, and thus no alien compounds are introduced which will accumulate or otherwise need to be removed.

To realize the objectives of this invention of reducing energy consumption while at the same time maintaining a melamine product of acceptable purity, the portion of the residual aqueous stream subjected to the purification treatment will generally be in the range of between about 5 and 50 percent of the total residual aqueous stream. More preferably, between about 8 and 15 percent of this residual aqueous stream will be subjected to the purification treatment.

The improvement of this invention is applicable to any known method for preparing melamine from urea or thermal decomposition products. These methods can generally be classified as either high-pressure or medium or low-pressure processes.

In the high-pressure processes, melamine is prepared from urea at a pressure of more than 50 bar, without a catalyst, and a reaction mixture of molten melamine, ammonia and carbon dioxide is formed. This reaction mixture can be cooled with water or an aqueous solution, either simultaneously with the reduction of pressure of this mixture, or thereafter. In order to optimize the heat balance and water balance in this process as a whole, it is generally preferable to utilize as the cooling medium a recycle solution from a later phase in the process, for example, mother liquor remaining after the crystallization and removal of product melamine.

In the medium and low-pressure processes, melamine is prepared by the conversion of urea in the presence of a catalyst at a pressure generally between 1 and 25 bar, and preferably between 1 and 10 bar. At least a part of this conversion generally takes place in a fluidized bed in the presence of ammonia and possibly also carbon dioxide. Catalysts commonly used in such medium or low-pressure processes include silica, alumina, silica-alumina, titanium oxide, zirconium oxide, boron phosphate, aluminium phosphate, or mixtures of two or more of these compounds.

The melamine-containing reaction mixture formed in low or medium-pressure processes is in a gaseous form and contains, in addition to melamine, ammonia, carbon dioxide, and generally small amounts of gaseous impurities. This gaseous reaction mixture may also contain a small amount of catalyst carried over from the reactor.

Where a wet catch method of recovering melamine from the reaction mixture is utilized, the gas mixture is quenched or cooled with an aqueous medium, such as water or an aqueous solution, after it leaves the melamine reactor. Depending on the amount of water utilized, this yields either a melamine solution or a suspension of melamine particles in water. Thereafter, further purification of the melamine product can be effected by recrystallization to obtain the final product melamine.

According to one preferred mode of carrying out this improved process, a concentrated suspension of solid melamine particles is formed in a saturated melamine solution by quenching or cooling the melamine-containing reaction mixture with an aqueous medium in a wet catching system. The resulting suspension is subsequently diluted with recycled residual aqueous liquid, for example, from the crystallization section, which may be either untreated or purified in accordance with this invention. As a result of the dilution, and if necessary the application of heat, the melamine particles dissolve to form a concentrated melamine solution. If desired, this solution can be filtered to remove any remaining particles, such as catalyst. The solution is thereafter fed to the crystallization section wherein product melamine is formed and separated from a residual aqueous liquid stream. A portion of this residual aqueous stream is then subjected to the purification treatment in accordance with this invention. For instance, the liquid overflow from the crystallizer, which is substantially free of solid melamine, can advantageously be wholly or partially fed into the purification system.

Preferably, both the purified and the untreated residual aqueous streams are recycled to the process, either separately or combined. Generally, this recycled residual aqueous stream is used to cool the melamine-containing reaction mixture. However, it is also possible to return parts of this residual aqueous stream to various different sections of the process.

By carrying out the process with the improvement as described above, the melamine-containing solution or suspension can be kept at a high pH value until the solid melamine product is separated out. At these higher pH values, the main impurities remain dissolved in the solution so that they will not appear in the end product. Thereafter, only a minor portion of the residual aqueous stream or motor liquor need be reduced in pH to effect the precipitation of impurities, with the result that after the impurities have been filtered out, the pH of the purified stream need not be adjusted before being recycled into the process. Nevertheless, sufficient impurities can be removed in this manner so as to stabilize the amount of impurities within the circulating liquid stream at a level sufficiently low to still permit crystallization and separation of substantially pure melamine product.

DETAILED DESCRIPTION OF THE DRAWING

The improved process will be explained with reference to the drawing which schematically illustrates one preferred mode of realizing the improved process of the invention.

Liquid urea is fed into melamine reactor 1 through line 2. Reactor 1 contains a fluidized bed of catalyst particles, for example silica, which bed is maintained in a fluidized state by means of gaseous $NH_3$ supplied through line 3. Hot molten salt is introduced through line 4 into heating salt coils 5 which maintain the fluidized bed at a sufficiently high temperature to effect the conversion of urea to melamine. This molten salt is heated in furnace 9 and fed via line 4 into salt coils 5 located within the fluidized bed. After transferring a portion of its heat to the fluidized bed, the cooled molten salt is returned, via line 6, tank 7 and line 8, to furnace 9 wherein it is reheated.

A reaction mixture containing melamine, ammonia and carbon dioxide leaves reactor 1 through line 10 and is introduced into columns 11 and 12 wherein the hot gas mixture is quenched and cooled by means of aqueous solutions fed through lines 13, 14 and 77, to form an aqueous suspension of solid melamine particles. This aqueous suspension is discharged from the bottom of column 12 via pump 15 and line 16 and fed into hydrocyclone 17 wherein it is concentrated. The lean melamine suspension leaving hydrocyclone 17 through line 13 is returned to columns 11 and 12, while the more concentrated melamine suspension or slurry formed in hydrocyclone 17 is fed via line 18 into desorption column 19.

In desorption column 19, a part of the ammonia and carbon dioxide dissolved in the suspension is desorbed by the application of heat, and the gas mixture thus formed is returned to column 12 through line 20.

The suspension leaving the bottom of desorber 19 via line 21 is fed into dissolving vessel 22 wherein it is mixed with filter aid introduced through line 23 and mother liquor introduced through line 24. The resulting mixture is transferred to dissolution vessel 30 (via line 25, pump 26, heater 28 and line 29) wherein the melamine dissolves in the liquor to form a concentrated melamine solution. This melamine solution is then introduced via line 31 into filter 32 wherein any solid impurities and catalyst particles still present in the liquid are filtered off. The filtered melamine solution is then fed via line 33 into recycling line 34 of crystallizer 35. A portion of the crystallizer contents is continuously recycled through line 36, pump 37, and line 34.

A portion of the suspension of melamine crystals is withdrawn from line 36 through line 38 and fed via pump 39 and line 40 into hydrocyclone 41. The substantially crystal-free overflow of hydrocyclone 41 is fed via line 42 to mother liquor vessel 43. The substantially crystal-free overflow from crystallizer 35 is also fed, via line 44, into mother liquor vessel 43.

A vacuum is maintained in crystallizer 35 by means of a vacuum unit (not shown in the drawing) which is connected to the crystallizer via line 45, cooler 46 and line 48. The condensate formed in cooler 46 is fed into line 49 which will be described further below.

The concentrated suspension of melamine crystals formed in hydrocyclone 41 is fed through line 50 into centrifuge 51 wherein substantially all of the remaining water is removed from the melamine crystals. The virtually water-free crystals are then introduced into dryer 53 through line 52 and therein dried with the aid of hot air supplied through line 54. The dried melamine crystals are separated from the air in cyclone 55 and the air is discharged via line 56, bag filter 57, line 58, blower 59 and line 60. The dry melamine product separated in cyclone 55 and collected in bag filter 57 is sent to storage (not illustrated) through lines 62 and 61, respectively, and through line 63.

The mother liquor collected in mother liquor vessel 43 is discharged via line 64, pump 65 and line 66. A portion of this mother liquor is fed via line 67 into the mother liquor purification section beginning with vessel 69.

In vessel 69, the mother liquor is dosed with $CO_2$ fed through line 70 in order to reduce its pH. The mother liquor discharged from vessel 69 is fed via line 71 into heater 72, and via line 73 into dissolution vessel 74. The mother liquor is then fed via line 75 into filter 76 wherein precipitated by-product impurities are filtered out, and the purified mother liquor is introduced via line 77 into columns 11 and 12 wherein the reaction mixture is quenched and cooled.

The remainder of the mother liquor from mother liquor vessel 43, which is not treated in the purification section, is either fed directly to columns 11 and 12 via line 14 to quench and cool the reaction mixture, or is fed to dissolving vessel 22 via line 49, heat exchanger 68 and line 24.

In heat exchanger 68, the mother liquor exchanges heat with a hot gas mixture coming from column 12 via line 78. During this exchange of heat, part of the gas mixture condenses, and the condensate and the uncondensed gas are fed to absorption column 81 through lines 79 and 80, respectively.

Liquid $NH_3$ is fed to the top of absorption column 81 from an external source (not illustrated) to condense any remaining carbon dioxide out of the substantially pure ammonia gas which leaves column 81 via line 82. This ammonia gas is recycled to melamine reactor 1 (via compresser 83, line 84, heater 85 and line 3) wherein it is used as the fluidization gas. A dilute solution of ammonium carbamate is discharged from the bottom of absorption column 81 via line 86, pump 87, and line 88.

DETAILED DESCRIPTION OF A PREFFERED EMBODIMENT

A preferred embodiment of the improvement of this invention will be elucidated by means of the following example.

In the apparatus as shown in the Figure, 24,320 kg/h of liquid urea was fed into melamine reactor 1 through line 2. From this reactor, a reaction gas mixture consisting substantially of melamine, ammonia, and carbon dioxide, was discharged through line 10.

After the gas mixture had been cooled in columns 11 and 12, the aqueous suspension of solid melamine in a saturated melamine solution thus obtained was substantially freed of ammonia and carbon dioxide in desorption column 19, and diluted with mother liquor in dissolving vessel 22. Thereafter, the concentrated melamine solution was filtered, crystallized, and separated from the residual aqueous liquid stream. The product melamine thus produced, after drying, amounted to 8,000 kg/h.

The overflow from crystallizer 35 via line 44, and the overflow from hydrocyclone 41 via line 42, were sent to mother liquor vessel 43 at a total rate of 359,770 kg/h. This mother liquor contained 2.0 percent by weight melamine and 0.2 percent by weight dissolved by-products. Of this total amount of mother liquor, 9.6 percent was fed to vessel 69 of the purification section through line 67. In vessel 69, about 82 kg/h of carbon dioxide was introduced, which lowered the pH of the mother liquor from 9.5 to 8.3. After heating in order to dissolve any remaining solid melamine particles, part of the by-product impurities which had precipitated were filterd off. The thus treated mother liquor was subsequently recycled to columns 11 and 12 wherein it was used to cool a further quantity of the hot reaction mixture.

When proceeding in this manner, it has been found that by subjecting only a small portion of the mother liquor to the purification treatment, by-product impurities are removed from the process to a sufficient degree to prevent their buildup in the recirculating streams and to permit the crystallization and separation of a substantially pure melamine product. The melamine obtained by this process contained at least 99.8 percent melamine, and so few by-products that all specifications regarding color and reactivity were met.

What is claimed is:

1. In a process for the preparation of melamine from urea or thermal decomposition products thereof wherein a reaction mixture is cooled with an aqueous medium to form an aqueous product stream containing melamine and reaction by-products, whereafter product melamine is separated from said aqueous product stream leaving a residual aqueous stream which is recycled into said process, the improvement wherein a portion of said residual aqueous stream still containing reaction by-products is separated from the remainder of such stream and is treated to remove by-products therefrom prior to being recycled to said process.

2. The process of claim 1 wherein the portion of said residual aqueous stream treated constitutes between about 5 and 50 percent of said stream.

3. The process of claim 2 wherein the portion of said residual aqueous stream treated constitutes between about 8 and 15 percent of said stream.

4. The process of claim 1, 2, or 3 wherein the portion of said residual aqueous stream is treated by lowering its pH to a level of between about 7.5 and 9.0 to form a precipitate of said by-products, and said precipitate is removed therefrom by filtration.

5. The process of claim 4 wherein said pH is lowered by the addition of carbon dioxide.

6. The process of claim 1 wherein the treated portion of said residual aqueous stream is recycled into said process as at least a part of said aqueous medium used for cooling said reaction mixture.

7. The process of claim 1 wherein the remainder of said residual aqueous stream is recycled into said process as at least a part of said aqueous medium used for cooling said reaction mixture.

8. The process of claim 1 wherein said reaction mixture is cooled with said aqueous medium to form an aqueous suspension of melamine particles, whereafter said suspension is diluted with recycled residual aqueous stream and said melamine particles substantially all dissolved to form said aqueous product stream.

9. The process of claim 8 wherein said suspension is diluted with the treated portion of said recycled aqueous stream.

10. The process of claim 8 wherein said suspension, after dilution, is heated to promote the dissolution of said melamine particles.

11. The process of claim 8, 9, or 10 wherein melamine is crystallized and removed from said aqueous product stream, and a portion of the residual aqueous stream thus formed, substantially free of solid melamine particles, is subjected to said treatment for removal of by-products.

12. The process of claim 11 wherein said aqueous prouduct stream is filtered prior to said crystallization to remove particles suspended therein.

* * * * *